United States Patent [19]
Rhodes

[11] Patent Number: 5,378,044
[45] Date of Patent: Jan. 3, 1995

[54] TAPE WRAPPING APPARATUS

[76] Inventor: Sidney R. Rhodes, P.O. Box 56, Karnes City, Tex. 78118

[21] Appl. No.: 163,394

[22] Filed: Dec. 6, 1993

Related U.S. Application Data

[63] Continuation of Ser. No. 852,017, Mar. 16, 1992, abandoned.

[51] Int. Cl.6 ............................................. A47C 7/50
[52] U.S. Cl. ........................... 297/423.25; 297/188.01
[58] Field of Search ............... 52/8, 9, 10; 297/423.1, 297/423.19, 423.2, 423.21, 423.22, 423.23, 423.25, 423.26, 423.27, 423.38, 188, 192

[56] References Cited

U.S. PATENT DOCUMENTS

| | | | |
|---|---|---|---|
| 38,718 | 5/1863 | Watson et al. | 297/423.20 |
| 165,498 | 7/1875 | Ott | 297/423.21 X |
| 183,924 | 10/1876 | Harrison | 297/423.21 X |
| 590,268 | 9/1897 | Lee | 297/437 X |
| 606,691 | 7/1898 | Springer | 297/437 X |
| 669,156 | 3/1901 | Archer | 297/423 X |
| 1,379,766 | 5/1921 | Koblos | 108/28 |
| 1,593,557 | 7/1926 | Armbruster | 108/28 |
| 1,817,878 | 8/1931 | Clements, Jr. | 297/188 X |
| 2,084,854 | 6/1937 | McCarthy | 108/28 X |
| 2,136,354 | 11/1938 | Welsh | 297/423 X |
| 2,495,374 | 1/1950 | Horn | 297/423.21 X |
| 2,628,879 | 2/1953 | Schultz | 297/192 X |
| 2,723,788 | 11/1955 | Lund | 297/192 X |
| 3,974,894 | 8/1976 | Wenger et al. | 182/152 X |
| 4,427,234 | 1/1984 | Peters | 297/437 X |

FOREIGN PATENT DOCUMENTS 1596919  9/1981  United Kingdom ............. 297/423.2

Primary Examiner—Peter R. Brown
Assistant Examiner—Milton Nelson, Jr.
Attorney, Agent, or Firm—Vaden, Eickenroht, Thompson, Boulware & Feather

[57] ABSTRACT

There is disclosed an apparatus for facilitating the wrapping of tape by a first individual about the ankle of a second individual, wherein the second individual is seated upon a first seating surface of an upright stand with the calf of the second individual supported on another surface forwardly of the front surface to dispose the ankle in position to be wrapped by the first individual while standing in front of the stand.

8 Claims, 2 Drawing Sheets

TAPE WRAPPING APPARATUS

This application is a continuation of application Ser. No. 07/852,017, filed on Mar. 16, 1992 and now abandoned.

This invention relates generally to apparatus for facilitating the wrapping of tape by a first individual about the ankle a second individual.

To prepare for football and other athletic endeavors, it is often necessary to tape the ankles of the participants. Ordinarily, this requires that another individual wrap the tape about the ankle of the participant's leg while the latter is seated on a bench on or other relatively low surface. Even when the leg is extended, it's necessary that the individual be in a bent over position while applying the tape. This is not only uncomfortable, but also can cause strain and other severe back problems, especially when it is necessary to apply tape to a large number of ankles.

The primary object of this invention is to provide relatively simple and inexpensive apparatus on which the individual whose ankle is to be taped may be seated to permit the other individual to apply the tape without supporting the leg and while in an upright and otherwise comfortable position.

Another object is to provide such apparatus which requires a minimum of space, but which, at the same time, is so constructed and arranged as to enable the individual to be taped to move with ease into and out of seated position.

A more particular object is to provide such apparatus which further facilitates the taping procedure by making the tape and other equipment to be used easily accessible to the individual applying it.

These and other objects are accomplished, in accordance with the illustrated and preferred embodiment of the invention, by apparatus which comprises an upright stand having front and back sides and opposite ends, means forming a first surface extending across the stand near the back thereof on which the second individual may be seated, and means forming a second surface extending across the stand forwardly of the first surface to support the calf of a leg of the seated individual to dispose the ankle in position to be wrapped by the first individual while standing in front of the stand. More particularly, the first and second surfaces are spaced from one another to provide a walkway through which the second individual may move into and out of seated position, and means are provided on the side of the stand by which the second individual may climb onto or climb down from the walkway.

In the preferred embodiment, means are also provided across the front of the stand on which rolls of tape may be supported for access by the second individual. More particularly, the means for supporting the tape is on a shelf of the stand generally beneath the ankle of the second individual, and, as illustrated, comprise upright posts over which the rolls may be placed. In the preferred embodiment, the seating surface is padded, and a means is provided for adjusting the height of the second supporting surface, so as to arrange the ankle to be taped at the most correction level for both individuals.

In the drawings, wherein like reference characters are used throughout to designate like parts:

Figure 1:
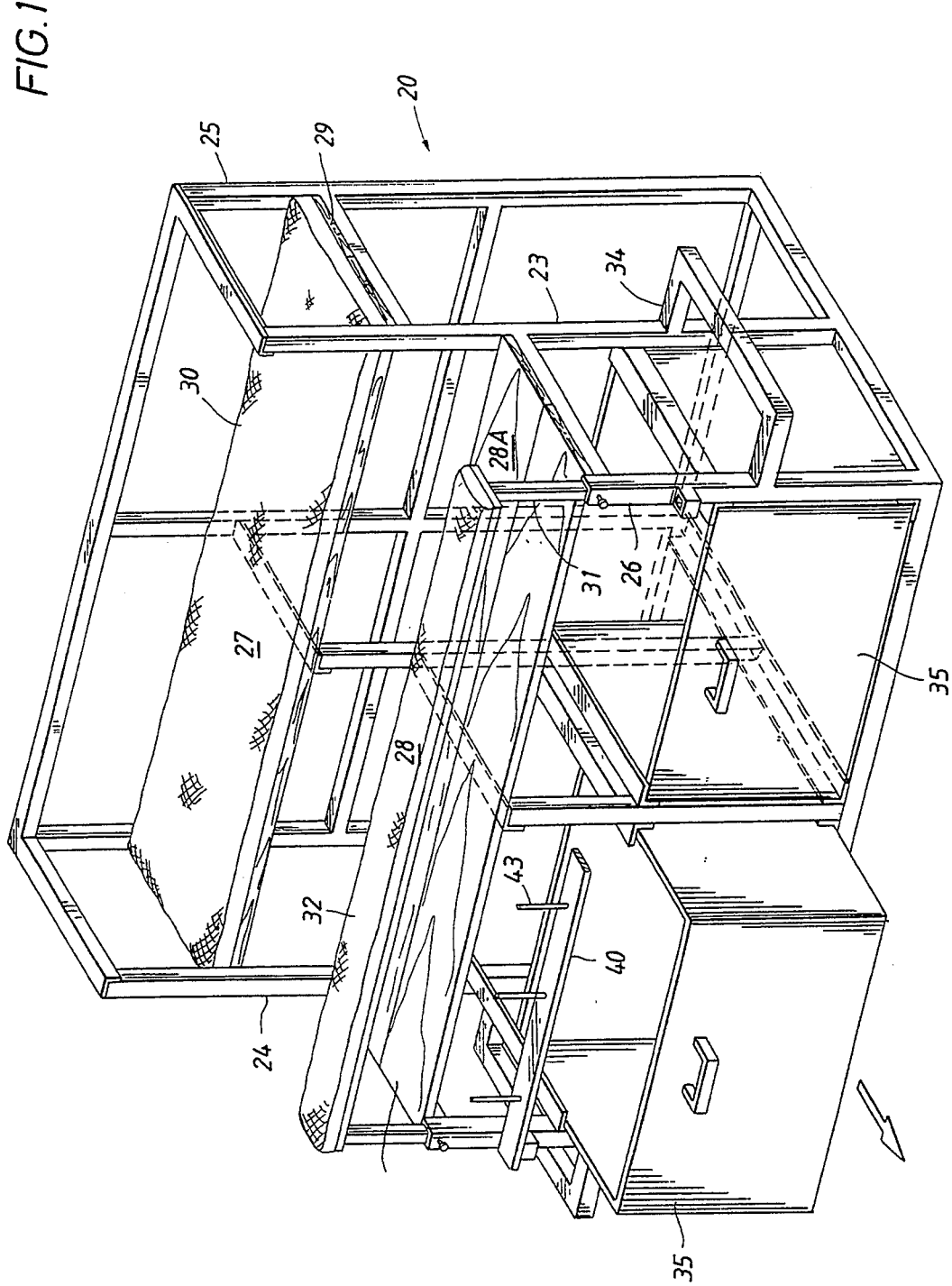
FIG. 1 is a perspective view of apparatus constructed in accordance with the present invention, as seen looking downwardly from the front side and one end thereof, and showing the shelf on which the rolls of tape are mounted broken away in part.

With reference now to the details of the above described drawings, the overall apparatus shown in FIG. 1, and indicated by its entirety by reference character 20, comprises an upright stand having an open framework which is generally rectangular in plan and supported on a suitable surface in the athletic facility in an upright position. The framework is made up of square tubing and angles connected to one another to form front and rear sides 21 and 22 and opposite ends 23 and 24 to form rear section 25 somewhat taller than a front section 26. More particularly and as will be described in detail to follow, the rear section has a surface 27 on which the individual to be tapped is seated, the front section has a surface 28 on which the calf of the individual may be supported (see FIG. 1) forwardly and beneath the seating surface to permit the individual to pass into and out of seated position.

The seating surface includes a wooden slab 29 which extends between the ends of the framework, and a padded cushion 30 which covers the slab. The vertically extending tubular parts of the sides of the ends of the rear section of the framework extend upwardly beyond the seating surface and are connected by a laterally extending member along the rear of the framework to form a back support and end rails for the individual seated on the seating surface.

The calf supporting surface is, on the other hand, adjustably supported at the front of the stand so as to accommodate the most comfortable position of the individual's leg. For this purpose, the surface includes a relatively narrow, laterally extending slab having vertical legs 31 which are received within hollow vertical columns at the corners of the front section of the framework. More particularly, the surface is adjusted vertically by means of set screws which are received in the corner columns for tightly engaging the legs. As also shown, the upper surface of the seating surface includes a cushion 32 mounted on the laterally extending slab.

Boards or slabs 33 are supported on the top of the front section walkway (28) intermediate the seating and calf supporting surfaces. As shown, this walkway is lower than the calf supporting surface and provides access to and from seated position on the framework.

Access to the walkway is facilitated by a ladder 34 in the form of a U-shaped tubing on each end of the front section of the stand generally intermediate its upper and lower ends. As the individual moves onto and off of the seated surface, and while climbing the ladder, he may of course grab the front column of the rear section to steady himself.

Figure 2:
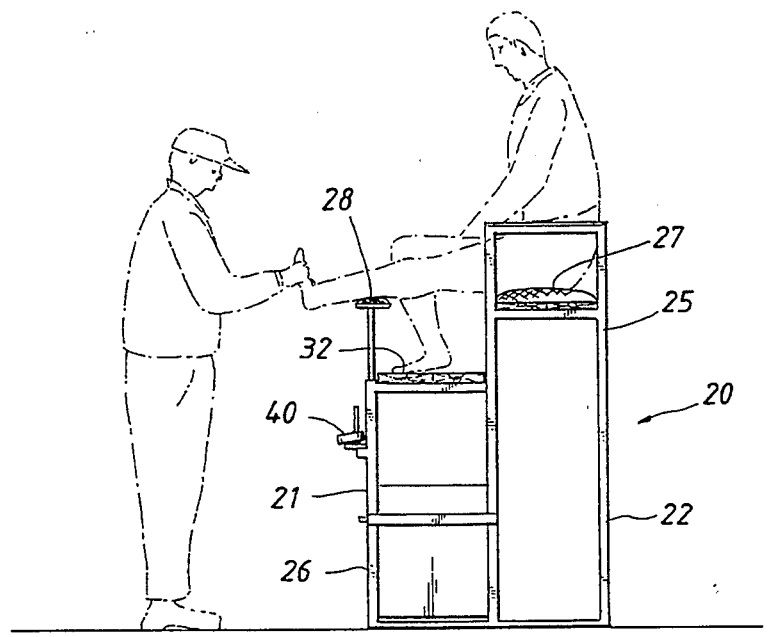
FIG. 2 is a view of one end of the apparatus shown in FIG. 1, on a reduced scale, and showing a first individual seated thereon with his leg supported in position to dispose the ankle in the position to be taped by a second individual standing at the front of the apparatus.

As shown, the stand is preferably of such width from one end to the other as to accommodate two or more persons, such that the ankles of both may be taped at generally the same time. As best shown in FIG. 2, the height of the framework, and particularly the calf supporting surface, is such that the ankle of the individual to be taped is easily accessible to the individual who is doing the taping while in an upright position. Thus, for example, the walkway may be 2½ to 3 feet high, and the seating surface 3½ to 4 feet high, with the adjustable top of the cam supporting surface being somewhere in between. In this way, the walkway not only permits the individual to be taped to climb on to and climb down from the seating surface with the least amount of effort, but also to comfortably support the leg whose ankle is not being taped, as can be seen from FIG. 2.

As best shown in FIG. 1, a shelf 40 is supported on stub flanges formed on the front corner columns of the framework somewhat beneath the elevation of the walkway. For this purpose, the shelf has pins 42 on its lower side adapted to be received in holes in the flanges. As previously described, and as shown, posts 43 extend upwardly form the shelf in spaced-apart relation so as to receive rolls of tape for easy access by the taping individual.

As shown in FIG. 1, the front section has angles secured to its corner members in position to provide rails for receiving drawers 35 movable into and out of the open space in the front section beneath the walkway. These drawers may of course provide storage space for other equipment used in the taping facility.

Figure 3:
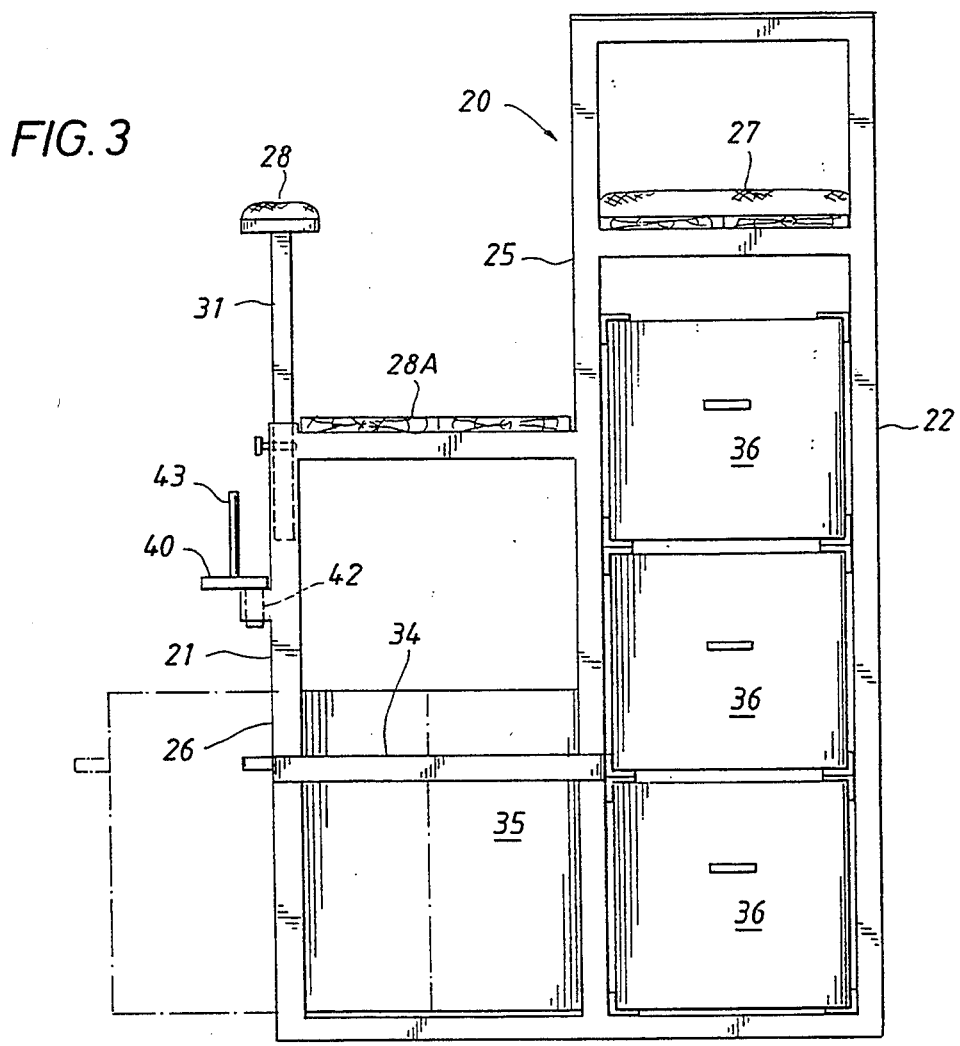
FIG. 3 is another end view similar to FIG. 2, but on an enlarged scale, of a modified embodiment of the apparatus.

In a similar manner, and as shown in FIG. 3, the opposite ends of the rear section have angles so mounted thereon as to form three sets of vertically spaced rails for accommodating vertically arranged drawers 36. Thus, in this case, the three drawers would occupy the space beneath the seating surface of the rear section.

As shown in FIG. 1, the side drawers have been eliminated so as to better illustrate the construction of the framework. However, both the front and side drawers are shown installed in FIG. 3.

From the foregoing it will be seen that this invention is one well adapted to attain all of the ends and objects hereinabove set forth, together with other advantages which are obvious and which are inherent to the apparatus and structure.

It will be understood that certain features and subcombinations are of utility and may be employed without reference to other features and subcombinations. This is contemplated by and is within the scope of the claims.

Because many possible embodiments may be made of the invention without departing from the scope thereof, it is to be understood that all matter herein set forth or shown in the accompanying drawings is to be interpreted as illustrative and not in a limiting sense.

What is claimed is:

1. Apparatus for facilitating the wrapping of a tape by a first individual about the ankle of a second individual, comprising an upright stand having front and back sides and opposite ends, means forming a first elongate surface extending laterally across the stand near the back side thereof for supporting a second seated individual, wherein the back side extends above the level of the first elongate surface means forming a second elongate and relatively horizonal surface extending laterally across the stand forwardly of the first surface and on generally the same level as that first surface for supporting the calf of a leg of the second individual with the ankle in position to be wrapped by the first individual while standing in front of the stand and spaced forwardly of the first surface, and means forming a laterally elongate walkway intermediate the space between the first and second surfaces for facilitating movement of the second individual into and out of a seated position on the first surface.

2. Apparatus of the character defined in claim 1, including means on an end of the stand by which the second individual may climb onto or climb down from the walkway.

3. Apparatus of the character defined in claim 1, wherein the first surface is padded.

4. Apparatus of the character defined in claim 1, including means for adjusting the height of the second supporting surface.

5. Apparatus of the character defined in claim 1, including a backrest on the back side of the stand and rearwardly of the first elongate surface.

6. Apparatus of the character defined in claim 1, including means across the front side of the stand on which rolls of tape may be supported for access by the first individual.

7. Apparatus of the character defined in claim 3, wherein the means for supporting the rolls of tape is on a shelf of the stand generally beneath and forwardly of the second surface.

8. Apparatus of the character defined in claim 7, wherein the tape supporting means comprises upright posts over which the rolls may be placed.

* * * * *